(12) United States Patent
Norburn

(10) Patent No.: US 7,354,573 B2
(45) Date of Patent: Apr. 8, 2008

(54) SHAVING, AFTER-SHAVE, AND SKIN CONDITIONING COMPOSITIONS

(76) Inventor: Robert B. Norburn, 4. Farleigh Close, Westhoughton, Bolton (GB) B15 3ES ( * ) Notice: Subject to any disclaimer, the term of this patent is extended or adjusted under 35 U.S.C. 154(b) by 536 days.

(21) Appl. No.: 10/349,116

(22) Filed: Jan. 23, 2003

(65) Prior Publication Data

US 2003/0143253 A1   Jul. 31, 2003

Related U.S. Application Data

(60) Provisional application No. 60/352,571, filed on Jan. 31, 2002.

(51) Int. Cl.
*A61Q 9/02* (2006.01)
*A61K 8/00* (2006.01)
*A61K 65/00* (2006.01)

(52) U.S. Cl. .................. 424/73; 424/59; 424/766

(58) Field of Classification Search ............ 424/73
See application file for complete search history.

(56) References Cited

U.S. PATENT DOCUMENTS

| | | | |
|---|---|---|---|
| 4,608,392 A | | 8/1986 | Jacquet et al. |
| 4,784,849 A | | 11/1988 | Tutsky |
| 5,278,106 A | * | 1/1994 | Nakashima et al. ......... 501/12 |
| 5,345,680 A | | 9/1994 | Vreeland et al. |
| 5,880,076 A | * | 3/1999 | Vermeer ............... 510/123 |
| 5,902,574 A | | 5/1999 | Stoner et al. |
| 6,143,288 A | * | 11/2000 | Warren et al. ............... 424/84 |
| 6,264,963 B1 | | 7/2001 | Leifheit et al. |

| | | |
|---|---|---|
| 6,342,208 B1 | | 1/2002 Hyldgaard et al. |

FOREIGN PATENT DOCUMENTS

| | | |
|---|---|---|
| CA | 1244350 | 11/1988 |
| EP | 624363 | 11/1994 |
| EP | 974639 | 1/2000 |
| EP | 1174108 | 1/2002 |
| FR | 1428054 | 1/1966 |
| FR | 1463171 | 12/1966 |
| FR | 2314706 | 1/1977 |
| FR | 2635682 | 3/1990 |
| FR | 2789397 | 8/2000 |
| GB | 429786 | 6/1935 |
| GB | 454658 | 11/1936 |
| GB | 1530064 | 10/1978 |
| JP | 08310927 A * | 11/1996 |
| WO | WO 98/20852 | 5/1998 |
| WO | WO 9832454 A1 * | 7/1998 |

OTHER PUBLICATIONS

XP002239624; CAS abstract accession No. 2000:136239.
XP002239626; Derwent WPI abstract accession No. 1985-294384.
XP002239625; CAS abstract accession No. 2001:874631.
XP002239627; Derwent WPI abstract accession No. 1988-005065.

* cited by examiner

*Primary Examiner*—Michael G. Hartley
*Assistant Examiner*—Nabila G. Ebrahim
(74) *Attorney, Agent, or Firm*—Mark R. Malek, Esq.; Zies Widerman Sutch & Malek

(57) ABSTRACT

A skin care composition comprising about 20% to about 85% by weight water, about 2% to about 40% by weight stearic acid and about 2% to about 40% by weight glycerin, diglycerin, grapeseed oil or a combination thereof is described. The composition is particularly useful as a shaving cream.

4 Claims, No Drawings

SHAVING, AFTER-SHAVE, AND SKIN CONDITIONING COMPOSITIONS

This application claims the benefit of United States Provisional patent application U.S. Ser. No. 60/352,571 filed on Jan. 31, 2002.

FIELD OF THE INVENTION

The present invention is related to skin care products, particularly to shaving, after-shave and skin conditioning compositions.

BACKGROUND OF THE INVENTION

Except for the introduction of electrical or mechanical devices, shaving methods have changed little over the centuries, the traditional wet shave still being predominant. Attempts are made to soften the hair by the application of wetted soap lathers, foams, gels or oils of various natures to make the hair somewhat easier to cut. These pre-shaving applications do little if anything to alleviate the problems encountered when shaving, specifically, razor bumps (pseudo folliculitis barbae), razor burn (microscopic cuts that easily become infected or inflamed), nicking or more serious cutting of the skin, and premature wear on the cutting edge of the blade being used. The applications mentioned above (soap lathers, gels, etc) usually require the use of additional 'after-shave' products of one form or another to calm or condition the skin after shaving.

U.S. Pat. No. 4,608,392 describes the use of polyether oligomers in a skin care product.

U.S. Pat. No. 6,264,963 describes a skin care composition whose benefits are achieved by using petrolatum or mineral oil. Although this patent mentions "softening of the hair prior to cutting" it makes no claim or suggestion that their formula could be used for shaving.

U.S. Pat. No. 4,784,849 and corresponding Canadian Patent 1,244,350 describe skin care and shaving compositions comprising phospholipids.

U.S. Pat. No. 5,345,680 describes a shaving aid for wet razor comprising polymers.

U.S. Pat. No. 5,902,574 describes a shaving preparation that uses cysteamine.

British Patent 429,786 describes a shaving preparation comprising sulphonated oils.

British Patent 454,658 describes a shaving cream, however, there is no mention of the use of either glycerin or diglycerin.

BRIEF SUMMARY OF THE INVENTION

There is provided a skin care composition comprising about 20% to about 85% by weight water, about 2% to about 40% by weight stearic acid and about 2% to about 40% by weight of glycerin, diglycerin, grapeseed oil or a combination thereof, based on the composition's total weight.

Compositions of the present invention are useful as skin care products.

There is further provided a commercial package comprising a skin care composition of the present invention together with instructions for its use in caring for skin.

DETAILED DESCRIPTION OF THE INVENTION

The amount of water (preferably water which has been deionised, distilled or otherwise purified) utilized in the composition may vary dependent on the desired consistency/viscosity of the final product. Water is generally present in an amount of about 20% to about 85% by weight, more particularly from about 50% to about 75% by weight and even more particularly from about 55% to about 70% by weight of the total composition.

Stearic acid is a commercial product and may be obtained from a variety of sources well known to those skilled in the art. It is generally present in an amount of about 2% to about 40% by weight, more particularly from about 5% to about 35% by weight and even more particularly from about 15% to about 30% by weight of the total composition.

Glycerin and diglycerin are also commercial products and may be obtained from a variety of sources well known to those skilled in the art. When present in the composition, they are generally present in an amount of about 2% to about 40% by weight, more particularly from about 5% to about 25% by weight and even more particularly from about 10% to about 20% by weight of the total composition.

Grapeseed oil is also a commercial product and may be obtained from a variety of sources well known to those skilled in the art. When present in the composition, it is generally present in an amount of about 2% to about 40% by weight, particularly about 2% to about 20% by weight, more particularly from about 5% to about 15% by weight and even more particularly from about 10% to about 15% by weight of the total composition. Grapeseed oil is an anti-oxidant and may also help to lubricate during shaving. It is also a known and documented anti-carcinogen.

One of glycerin, diglycerin and grapeseed oil may be present individually in the composition, or a combination of two or more of glycerin, diglycerin and grapeseed oil may be present. It is possible to make glycerin and diglycerin from grapeseed oil by known processes. Any glycerin or diglycerin used in the composition may be made partially or entirely from grapeseed oil. This is especially useful when grapeseed oil itself is not used in the composition.

The composition may contain small amounts of other ingredients (generally 5% or less of total weight, although greater amounts are possible in some instances). Other ingredients include, but are not limited to, for example emulsifiers (e.g. glyceryl stearate), preservatives (e.g. grapefruit seed extract (GSE)), perfumes (e.g. Bergamot oil), colouring agents, UV blockers, skin protectants (e.g. zinc oxide and the like), insect repellents, medications, pH modifiers (e.g. sodium hydroxide), or a combination thereof. Typically, other ingredients may be present in an amount of less than 2% by weight, although, for example, an emulsifier may be present in an amount as much as 10% by weight and a preservative, for example GSE, may be present in an amount of about 0.1% to about 5% by weight, with an amount of about 0.1% to about 2% by weight GSE being normal in many applications. These ingredients are well known in the field of skin care and the proportions are established and known to those skilled in the art.

Preservatives may act as product stabilizers and/or as shelf life enhancers and/or as anti-microbials. While any suitable preservative may be used, grapefruit seed extract (GSE) is preferred since it is a natural organic ingredient rather than of synthetic origin. Grapefruit seed extract (GSE) is well known and widely used for its anti-bacterial, anti-fungal, anti-viral and disinfectant properties.

The composition of the present invention is easily formulated by methods known in the art. Generally, the ingredients may be blended in the desired proportions to form the composition and then packaged into a suitable container, together with instructions for its use. Furthermore, the composition is easily packaged as a non-pressurized product, safe for air travel.

In a particular embodiment, the composition of the present invention may be prepared in a stage-wise blending procedure. For example, a first phase containing stearic acid, and optionally grapeseed oil and glyceryl stearate, is heated and blended with a propeller mixer in a jacketed vessel, at a temperature that permits homogenisation, typically from about 60 degrees Celsius to about 80 degrees Celsius more particularly 70 degrees Celsius. A second phase containing water and glycerin and/or diglycerin, and optionally other ingredients such as grapefruit seed extract, is heated and blended with a propeller mixer in a separate jacketed vessel, at a mixing temperature that permits easy homogenisation, typically from about 60 degrees Celsius to about 80 degrees Celsius, more particularly about 70 degrees Celsius. Once both phases are homogeneous, the first phase may be added to the second phase by blending, for example with a Silverson™ type mixer, for a period of time to permit substantially thorough blending (e.g. for about 1 hour depending on batch size). If desired, a pH modifier may be added to the mixture of the first phase and second phase to adjust the pH to 6.0-6.5, and the mixture blended with a propeller mixer before blending in the Silverson™ type mixer. After mixing with the Silverson™ type mixer, the product may then be returned to a propeller mixer and blended until the product has cooled sufficiently to permit the addition of any other desired ingredients. A third phase containing any other desired ingredients may then be thoroughly dispersed in the product by introduction and blending as appropriate, and the product then left to cool.

The composition of the present invention preferably is used as a shaving lubricant, as an after-shave and/or as a skin conditioner that moisturises, conditions and/or protects the skin, leaving an invisible barrier that provides a pleasant and non-greasy tactile experience. The composition is particularly useful as a multi-purpose cream that not only provides a very comfortable and close shaving experience, but also acts as an after-shave, conditioning and protecting the skin. More particularly, the composition is useful as a shaving cream.

Advantageously, the composition may provide a high degree of lubricity for shaving, plus emollient and humectant properties when used to condition the skin. The compositions are easily applied and quickly absorbed by both the hair and the skin. The composition reduces the need for additional after-shave compositions, in particular, reducing or eliminating the need or reliance on alcohol used in many after-shave products.

The composition of the present invention softens the hair and lubricates the skin, reducing the drag or friction of the blade against the hair or the skin, making it much easier for a blade to cut the hair. The high lubricity provided by the composition reduces the incidence of razor bumps, razor burn, nicks and cutting of the skin whilst at the same time protecting the cutting edge of the blade from excessive wear thus extending the effective life of the razor. The composition being readily absorbed by the skin is less likely to be dragged off during repeated shaving strokes, as is the case when using soap lathers, foams or other similar products, therefore providing a better and less problematic shave. The composition reduces or eliminates the need for soaps, foams, gels and other pre-shave lubricants and also reduces or eliminates the need to use water when shaving.

Being a non-foaming application, the composition also allows a person shaving to see more readily where the blade is cutting, which is particularly appreciated by those who have a partial beard or moustache.

However, since the composition is an excellent skin conditioner, it may be used solely as such, if desired. In particular, the composition provides excellent skin hydration plus the additional benefit of reduction of TEWL (trans epidermal water loss).

To reduce the possibility of drying of the skin, irritation of the skin, dermatitis or any other adverse reactions associated with petroleum or mineral oils these ingredients have been intentionally avoided.

Animal products and or by-products are also intentionally excluded not simply to avoid known adverse skin reactions but also to avoid any (even theoretical) prospect of contracting a prion disease (e.g., BSE aka Mad Cow Disease) that could be present in animal products or by-products. Furthermore animal products and or by-products have been intentionally excluded to respect people's religious beliefs and lifestyle choices. The compositions are intended to be both Kosher and Halal. Peanut oil is intentionally avoided so as to eliminate the risk of severe or even fatal allergic reactions. The use of plant based ingredients responds to the demand from the general public for more natural and or organic products, versus chemical or synthetic ingredients.

Preferably, the composition is intentionally uncomplicated, the intent being to produce a less complex product, comprising a minimal number of ingredients. When compared to other skin care preparations, the composition of the present invention can dramatically reduce the number and amount of chemicals being applied to the skin. Furthermore, the nature of each ingredient is selected so that reasonably educated members of the general public could easily recognise, relate to, and feel comfortable with the selected ingredients. Being a less complex composition, people will more likely read the list of ingredients and be less intimidated by the basic nature of the contents. In addition, the composition has potential cost, convenience and ecological advantages of being a single-pack, non pressurized, multi-purpose product.

Thus, in particularly preferred embodiments, the composition consists essentially of water, stearic acid, and glycerin, diglycerin, grapeseed oil or a combination thereof.

In one preferred embodiment, the composition consists essentially of 2-15% stearic acid, 5-20% glycerin and/or 5-10% grapeseed oil, 2-10% glyceryl stearate, 0.5-5% grapefruit seed extract, sodium hydroxide to adjust pH to 6.0-6.5, and water (e.g. deionized) to 100% (i.e. the balance).

In another preferred embodiment, the composition consists essentially of 2-5% stearic acid, 5-10% glycerin, 5-10% grapeseed oil, 2-6% glyceryl stearate, 0.5-1% grapefruit seed extract, sufficient sodium hydroxide (<0.1%) to achieve a pH of 6.0-6.5, and water (e.g. deionized) to 100% (i.e. the balance).

All percentage amounts are by weight based on the total weight of the composition, unless stated otherwise.

EXAMPLES

Amounts listed in the Examples are expressed by weight based on the weight of the total composition. The listed formulas (although intended as indicative) are presented as the presently preferred ingredient content, accurate within plus or minus 5%.

Formulas #1 to #4 were prepared by blending, as described previously (with glyceryl stearate or other appropriate and suitable emulsifier in an amount of 5% or less), the stated ingredients in the stated amounts. One skilled in the art can readily determine the amount of each ingredient in weight (mass) units by deciding upon the desired total weight and calculating the weight of each ingredient from the appropriate percentage listed in each Formula.

| Formula #1: Cream | |
|---|---|
| 15% | stearic acid |
| 20% | glycerin or diglycerin |
| 10% | grapeseed oil |
| <5% | glyceryl stearate |
| Balance | water |

| Formula #2: Cream | |
|---|---|
| 30% | stearic acid |
| 10% | glycerin or diglycerin |
| <5% | glyceryl stearate |
| Balance | water |

| Formula #3: Cream | |
|---|---|
| 25% | stearic acid |
| 15% | grapeseed oil |
| <5% | glyceryl stearate |
| Balance | water |

| Formula #4: Cream | |
|---|---|
| 5-10% | grapeseed oil |
| 2-15% | stearic acid |
| <5% | glyceryl stearate |
| 5-20% | glycerin/diglycerin |
| <2% | grapefruit seed extract |
| <2% | Bergamot oil |
| Balance | water |

Formula #5: Cream

A mixture of 15 kilograms grapeseed oil, 7.0 kilograms stearic acid and 8.0 kilograms glyceryl stearate SE (SE means self-emulsifying) were heated to 70° C. with good mixing using a propeller mixer to form Phase A. In a separate vessel, about 160 liters of deionized water was heated to 70° C. followed by the addition, with mixing, of 15 kilograms glycerin and 2 liters of grapefruit seed extract to form Phase B. Phase A and Phase B were then mixed together at 70° C. using a propeller mixer and sodium hydroxide was added in sufficient quantity to achieve a pH of 6.25. An emulsion was thereby formed. The resulting emulsion was mixed in a 200 kg capacity Silverson™ high shear mixer for 1 hour then returned to a propeller mixer and allowed to cool to 40° C. The mixer was turned off, the composition was covered and then was allowed to cool to room temperature. Once cooled to room temperature, the cream was transferred to containers for transport.

The cream of Formula #5 had the following composition:

| 7.5% | grapeseed oil |
|---|---|
| 3.5% | stearic acid |
| 4.0% | glyceryl stearate |
| 7.5% | glycerin |
| 1.0% | grapefruit seed extract |
| Balance | deionized water |

While the present compositions have been described with respect to what is at present considered to be the preferred embodiments, it is to be understood that invention is not limited to the disclosed embodiments. To the contrary, the invention is intended to cover various modifications, subtractions and or substitutions included within the spirit and scope of the appended claims.

The invention claimed is:

1. A shaving cream consisting of a mixture of:
   2-15% by weight stearic acid;
   5-20% by weight glycerin and/or 5-10% by weight grapeseed oil;
   2-10% glyceryl stearate;
   0.5-5% grapefruit seed extract;
   sodium hydroxide to adjust pH to 6.0-6.5; and
   balance water;
   all weights based on total weight of the composition;
   said stearic acid, glycerin, grapeseed oil, glyceryl stearate, grapefruit seed extract, sodium hydroxide, and water being combined to form a non-foaming mixture.

2. The shaving cream according to claim 1 wherein the stearic acid is present in an amount of 2% to 5% by weight.

3. The shaving cream according to claim 1 wherein the glyceryl stearate is present in an amount of 2% to 6% by weight.

4. The shaving cream according to claim 1 wherein the grapefruit seed extract is present in an amount of 0.5% to 1% by weight.

* * * * *